(12) United States Patent
Goodman et al.

(10) Patent No.: US 8,067,197 B2
(45) Date of Patent: Nov. 29, 2011

(54) SOLUBLE RECOMBINANT $\alpha_v\beta_3$ ADHESION RECEPTOR

(75) Inventors: Simon L. Goodman, Darmstadt (DE); Beate Diefenbach, Darmstadt (DE); Detelv Güssow, London (GB); Raj Mehta, Sudbury (GB); Eilish Cullen, London (GB); Alex Brown, Bucks (GB)

(73) Assignee: Merck Patent GmbH, Darmstadt (DE)

( * ) Notice: Subject to any disclaimer, the term of this patent is extended or adjusted under 35 U.S.C. 154(b) by 1267 days.

(21) Appl. No.: 10/460,672

(22) Filed: Jun. 13, 2003

(65) Prior Publication Data

US 2005/0130137 A1 Jun. 16, 2005

Related U.S. Application Data

(63) Continuation of application No. 08/987,756, filed on Dec. 9, 1997, now abandoned.

(30) Foreign Application Priority Data

Dec. 9, 1996 (EP) ..................................... 96119700

(51) Int. Cl.
*C12N 15/09* (2006.01)
*C07H 21/04* (2006.01)
(52) U.S. Cl. ...................................... 435/69.1; 536/23.1
(58) Field of Classification Search .................. None
See application file for complete search history.

(56) References Cited

U.S. PATENT DOCUMENTS

| | | | | |
|---|---|---|---|---|
| 4,223,002 | A | * | 9/1980 | Newman ........................ 436/542 |
| 4,745,051 | A | * | 5/1988 | Smith et al. ................. 435/69.51 |
| 5,212,071 | A | * | 5/1993 | Fearon et al. ................. 435/69.1 |
| 5,298,418 | A | * | 3/1994 | Granados ...................... 435/348 |
| 5,578,704 | A | * | 11/1996 | Kim et al. .................. 530/388.22 |
| 5,837,486 | A | * | 11/1998 | Bodary et al. ................ 435/69.1 |
| 5,854,205 | A | * | 12/1998 | O'Reilly et al. ................... 514/2 |
| 5,985,278 | A | * | 11/1999 | Mitjans et al. .............. 424/143.1 |

OTHER PUBLICATIONS

Fitzgerald et al 1987, J. Biol. Chem. 262, 3936 (β3).*
Suzuki et al. 1987, J. Biol. Chem. 262, 14080 (αv)).*
Mehta et al., Transmembrane-truncated alphavbeta3 integrin retains high affinity for ligand binding: evidence for an 'inside-out' suppressor? Biochem. J. 330:861-869, 1998.*
Marcinkiewicz et al., One-step affinity purification of recombinant alphavbeta3 integrin from transfected cells.Protein Expr. Purif. 8:68-74, 1996.*
Weinacker et al., Role of the integrin alpha v beta 6 in cell attachment to fibronectin. Heterologous expression of intact and secreted forms of the receptor. J. Biol. Chem. 6940-6948, 1994.*
Nishimura et al., Integrin alpha v beta 8. Interaction with vitronectin and functional divergence of the beta 8 cytoplasmic domain. J. Biol. Chem. 28708-28715, 1994.*
Wippler et al., The integrin alpha IIb-beta 3, platelet glycoprotein IIb-IIIa, can form a functionally active heterodimer complex without the cysteine-rich repeats of the beta 3 subunit. J Biol. Chem. 269:8754-8761, 1994.*

* cited by examiner

*Primary Examiner* — Ruixiang Li
(74) *Attorney, Agent, or Firm* — Millen, White, Zelano, Branigan, P.C.

(57) ABSTRACT

The invention relates to a novel purified recombinant $\alpha_v\beta_3$ adhesion receptor which shows an unimpaired ligand binding activity, and a process for preparing said soluble non-membrane bound receptor in excellent yields by recombinant techniques using a baculovirus-insect cell expression system. The so-synthesized soluble receptor may be used very easily as screening tool for new therapeutic compounds which may inhibit the natural $\alpha_v\beta_3$ adhesion receptor. Such therapeutic compounds which can be discovered very easily, fast and without health risk by means of the soluble receptors according to the invention may be, for example, RGD peptides or non-peptidic compounds mimicking the natural ligand epitopes. The invention relates, furthermore, to a corresponding process for preparing recombinant full-length $\alpha_v\beta_3$ adhesion receptor in excellent yields, additionally using detergents to dissolve the membrane bound receptor from the surface of the host cell.

6 Claims, 8 Drawing Sheets

SOLUBLE RECOMBINANT $\alpha_v\beta_3$ ADHESION RECEPTOR

TECHNICAL FIELD OF THE INVENTION

The invention relates to a novel purified recombinant $\alpha_v\beta_3$ adhesion receptor which shows an unimpaired ligand binding activity, and a process for preparing said soluble non-membrane bound receptor in excellent yields by recombinant techniques using a baculovirus-insect cell expression system.

The so-synthesized soluble receptor may be used very easily as screening tool for new therapeutic compounds which may inhibit the natural $\alpha_v\beta_3$ adhesion receptor.

The invention relates, furthermore, to a corresponding process for preparing recombinant full-length $\alpha_v\beta_3$ adhesion receptor in excellent yields, additionally using detergents to solve the membrane bound receptor from the surface of the host cell.

BACKGROUND OF THE INVENTION

Integrins are a super-family of cell surface adhesion receptors which control the attachment of cells with the solid extracellular environment both to the extracellular matrix (ECM), and to other cells. Adhesion is of fundamental importance to a cell; it provides anchorage and cues for migration and signals for growth and differentiation. Integrins are directly involved in numerous normal and pathological events, such as cell attachment, migration to blood clotting, inflammation, embryogenesis or cancer growth and metastasis, and as such, they are primary targets for therapeutic intervention.

Integrins are heterodimeric integral transmembrane glycoproteins, consisting of non-covalently linked $\alpha$ and $\beta$ subunits. The integrins are classified in four overlapping subfamilies, containing the $\beta_1$, $\beta_2$, $\beta_3$ or $\alpha_v$ chains, and a particular cell may express several different integrins from each subfamily.

The last decade has shown that integrins are major receptors involved in cell adhesion and so may be a suitable target for therapeutic intervention. Reports concerning integrins are given, e.g., by E. Ruoslahti (J. Clin. Invest., 1991, 87) and R. O. Hynes (Cell, 1992, 69).

The $\alpha_v$-series integrins are now seen to be a major subfamily, with both classical, and novel functions. In melanoma cell lines, for example, enhanced expression of the $\alpha_v\beta_3$ integrin correlated with tumorigenicity and metastatic properties (e.g. Felding-Habermann et al. 1992, J. Clin. Invest. 89, 2018; Marshall et al. 1991, Int. J. Cancer 49, 924), suggesting the involvement of $\alpha_v$-containing integrins in some steps of the tumor cell metastasis process. A similar role is discussed for carcinoma adhesion and spreading and colorectal cancer, respectively, which is one of the most common epithelial malignancies.

The $\alpha_v$-series integrins seem to exclusively recognize ligands bearing the RGD-($NH_2$-arginine-glycine-aspartic acid-COOH) tripeptide sequences, including those in vitronectin ($\alpha_v\beta_1$, $\alpha_v\beta_3$, $\alpha_v\beta_5$), fibronectin ($\alpha_v\beta_1$, $\alpha_v\beta_3$, $\alpha_v\beta_5$, $\alpha_v\beta_6$), and von Willebrand factor, fibrinogen, and osteopontin ($\alpha_v\beta_3$) (e.g., Busk et al. 1992, J. Biol. Chem. 267, 5790; Smith and Cheresh 1990, J. Biol. Chem. 265, 2168). Function blocking anti-integrin antibodies, e.g., antibodies directed against the $\alpha_v\beta_3$ integrin are also known (e.g., Cheresh and Spiro 1987, J. Biol. Chem. 262, 17703; Chuntharapai et al. 1993, Exp. Cell Res. 205, 345; EP 95 119 233).

The disruption of ligand-integrin interaction by peptides and antibodies has highlighted the important roles of $\alpha_v\beta_3$ integrin, "the vitronectin receptor," processes as diverse as tumor growth and metastasis, viral infection, osteoporosis and angiogenesis (Felding-Habermann and Cheresh 1993, Curr. Opin. Cell Biol. 5, 864; Brooks et al. 1994, Cell 79, 1157; Brooks et al. 1994, Science 264, 569). The emergence of $\alpha_v\beta_3$ as a potential target for therapeutic intervention has thus led to a search for $\alpha_v\beta_3$ antagonists—a process that requires purified $\alpha_v\beta_3$. The source of biochemical amounts of $\alpha_v\beta_3$ has usually been human placental tissue. In common with most integral membrane proteins, integrins can only be obtained as active solubilized molecules in the presence of non-ionic detergents and therefore purification of $\alpha_v\beta_3$ from placenta for drug screening is both cumbersome, costly, and a considerable health risk (Mitjans et al. 1995, J. Cell Sci. 108, 2825).

Although recombinant integrins have been expressed already in eukaryotic systems, such as in CHO cells (O'Toole et al. 1990, Cell Regul. 1, 883) and in embryonic kidney 293 cells (King et al. 1994, J. Bone Miner Res. 9, 381) the preparation of biochemically satisfactory amounts has not been achieved by recombinant technology.

There have been no reports on the biological activity of truncated soluble $\alpha_v\beta_3$ constructs, and full-length $\alpha_v\beta_3$ receptor apparently has not been produced by recombinant technology in biochemically important amounts.

Thus, it would be desirable to provide a soluble recombinant $\alpha_v\beta_3$ receptor which can be produced in biochemically useful amounts and in a purified quality by a comparably easy and riskless process. Moreover, such a process would be also advantageous for producing full-length $\alpha_v\beta_3$ receptor.

SUMMARY OF THE INVENTION

This invention describes for the first time high-level expression and purification of biologically competent soluble $\alpha_v\beta_3$ using the baculovirus-insect cell expression system. To achieve high yields of recombinant proteins processed in a manner similar to mammalian cells, over-expression of $\alpha_v\beta_3$ was achieved by utilizing the *baculovirus* polyhedrin gene as a strong viral promotor. The soluble molecule retains the ligand binding activity and specificity of the native placental and recombinant full length receptors, and can be purified in the absence of detergents, thus removing many possible ligation artifacts and producing a molecule suitable for high throughput screening and high resolution structural analysis.

Thus it is object of the present invention to provide an essentially purified soluble recombinant $\alpha_v\beta_3$ adhesion receptor with unimpaired ligand binding activity. A corresponding receptor which derives from human origin is a preferred embodiment of the invention.

The receptor according to the invention comprises the $\alpha_v$ chain and the $\beta_3$ chain of said receptor, each shortened at its C-terminus by a portion containing the transmembrane domain or a portion thereof and the complete cytoplasmatic domain of each individual chain. The amino acid and DNA sequences of the mature human $\alpha_v$ and $\beta_3$ protein chain as well their transmembrane and cytoplasmatic domains are known.

Especially, it is a preferred object of the invention to make available a soluble human recombinant receptor comprising a truncated $\alpha_v$ chain containing approximately 957 amino and a truncated $\beta_3$ chain containing approximately 692 amino acids, each calculated from the N-terminal of the corresponding mature protein chain. From this preferred soluble receptor the essentially complete transmembrane domain as well as the complete cytoplasmatic domain of the mature protein chains has been removed. However, the invention includes also soluble receptors comprising portions of the transmembrane domain (see below). The invention, however, is not limited to human $\alpha_V\beta_3$ receptor. According to the process described and claimed here it is no problem to generate $\alpha_V\beta_3$ receptors deriving from non-human origin.

Furthermore, a corresponding human receptor can be produced by the present invention which is obtainable by a process as defined below and in the claims. This process according to the invention provides highly purified soluble recombinant human $\alpha_V\beta_3$ adhesion receptor with unimpaired ligand binding activity in good yields, and is characterized by the following steps:

(i) a first cDNA coding for the $\alpha_V$ chain of said receptor, shortened by a portion comprising at least 52 amino acids calculated from the C-terminus, and a second cDNA coding for the $\beta_3$ chain of said receptor, shortened by a portion comprising at least 61 amino acids calculated from the C-terminus, is sub-cloned into a *baculovirus* transfer vector of a *baculovirus* expression system, (ii) said vector comprising said first and/or second DNA is transferred into the genomic DNA of a *baculovirus* of said expression system, (iii) insect cells are infected with said complete recombinant *baculovirus*, (iv) said infected insect cells are cultivated in a culture medium and said heteromeric truncated $\alpha_V\beta_3$ receptor is expressed into the medium, and (v) said receptor expressed is isolated from the medium and purified by antibody affinity chromatography, the antibody used hereby is specific to the human $\alpha_V\beta_3$ adhesion receptor or its individual component chains.

As another aspect of the invention a similar process for the preparation of recombinant full-length $\alpha_V\beta_3$ receptor, especially of human origin, is disclosed. This process is characterized by the following steps:

(i) a first cDNA coding for the complete $\alpha_V$ chain of said receptor and a second cDNA coding for the complete $\beta_3$ chain of said receptor, is sub-cloned into a *baculovirus* transfer vector of a *baculovirus* expression system, (ii) said vector comprising said first and/or second DNA is transferred into the genomic DNA of a *baculovirus* of said expression system, (iii) insect cells are infected with said complete recombinant *baculovirus*, (iv) said infected insect cells are cultivated in a culture medium, said cell membrane-bound receptor expressed is solubilized by a detergent, and (v) said solubilized receptor is purified from the cell-free medium by antibody affinity chromatography, the antibody used hereby is specific to the human $\alpha_V\beta_3$ adhesion receptor or its individual component chains.

The $\alpha_V\beta_3$ receptors according to the invention are optimally suitable for the screening of compounds, e.g., therapeutic compounds, which may inhibit the natural receptor. Therefore, the invention relates to the use of said soluble receptors for the discovery of said compounds. As mentioned above such compounds according to the invention are, above all, linear or cyclic peptides comprising one or more RGD units or they are non-peptidic analogues which show the same biological activities against the $\alpha_V\beta_3$ adhesion receptor as the RGD peptides (see below).

Finally the invention relates to a process of screening therapeutic compounds for their capability to inhibit the natural $\alpha_V\beta_3$ receptor by using said soluble $\alpha_V\beta_3$ receptor as defined above and below and a therapeutic compound, especially RGD-peptides or non-peptidic analogues thereof, which may inhibit said $\alpha_V\beta_3$ receptor.

Abbreviations:
$\alpha_V\beta_3$ integrin
17E6 mAb
AP3 mAb
LM609 mAb
P4C19 mAb
P1F6 mAb
$\alpha_V$ (FL) full-length $\alpha_V$ chain
$\alpha_V$ (SL) short-length (truncated) $\alpha_V$ chain
$\beta_3$(FL) full-length $\beta_3$ chain
$\beta_3$(SL) short-length (truncated) $\beta_3$ chain
BacPAK *Baculovirus* expression system
SF9, HighFive Insect cells
M.O.I. Multiplicity of Infection

BRIEF DESCRIPTION OF THE DRAWINGS

Various other features and attendant advantages of the present invention will be more fully appreciated as the same becomes better understood when considered in conjunction with the accompanying drawings, wherein.

Figure 7:
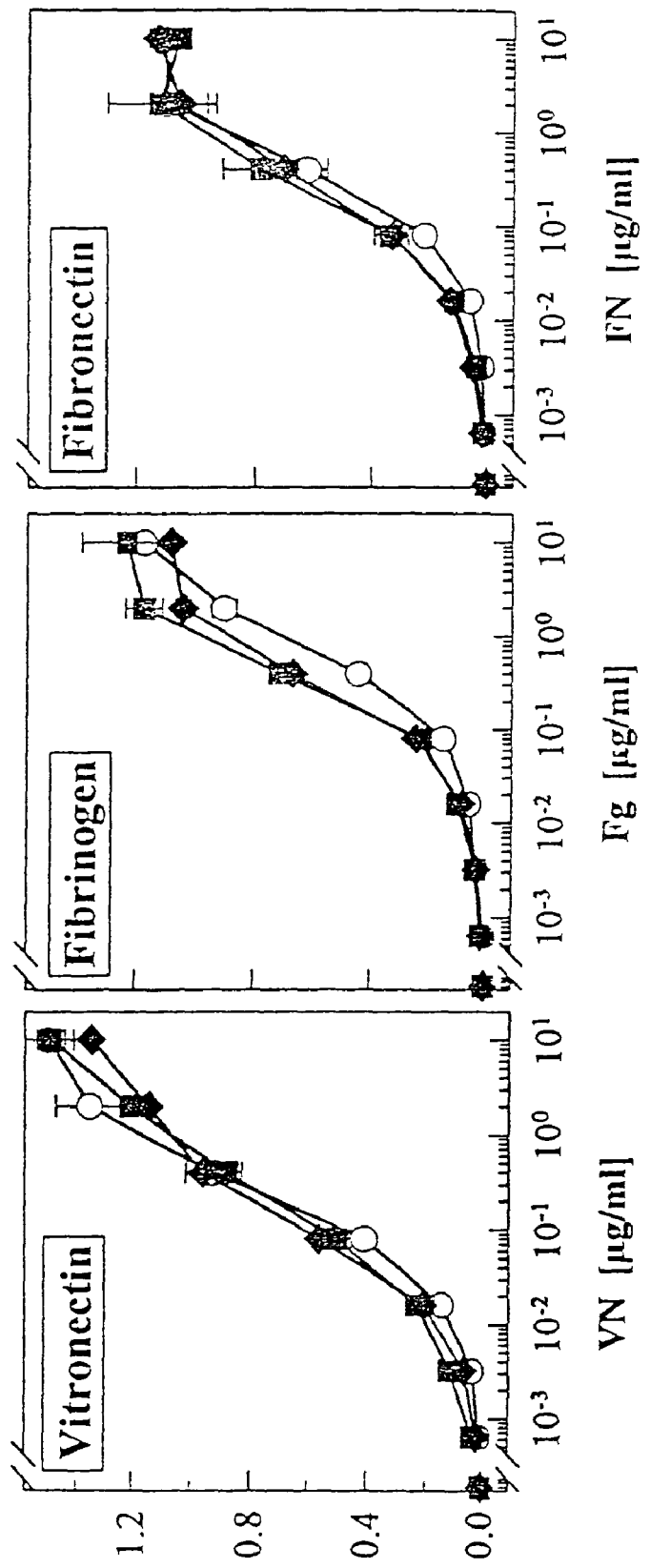

FIG. 7 shows activity test of purified recombinant $\alpha_V\beta_3$. Ligand binding to immobilized receptors: Biotinylated vitronectin, fibrinogen and fibronectin were allowed to bind to immobilized receptors. Bound ligand was detected using an anti-biotin antibody. Vertical axis: ligand binding in optical density units (405 nm), horizontal axis: vitronectin, fibrinogen, fibronectin concentration (µg/ml).
(○) $\alpha_V\beta_3$ placenta, (■) $\alpha_V$(FL)×$\beta_3$(FL), (♦) $\alpha_V\Delta$(SL)×$\beta_3\Delta$(SL).

Figure 8:
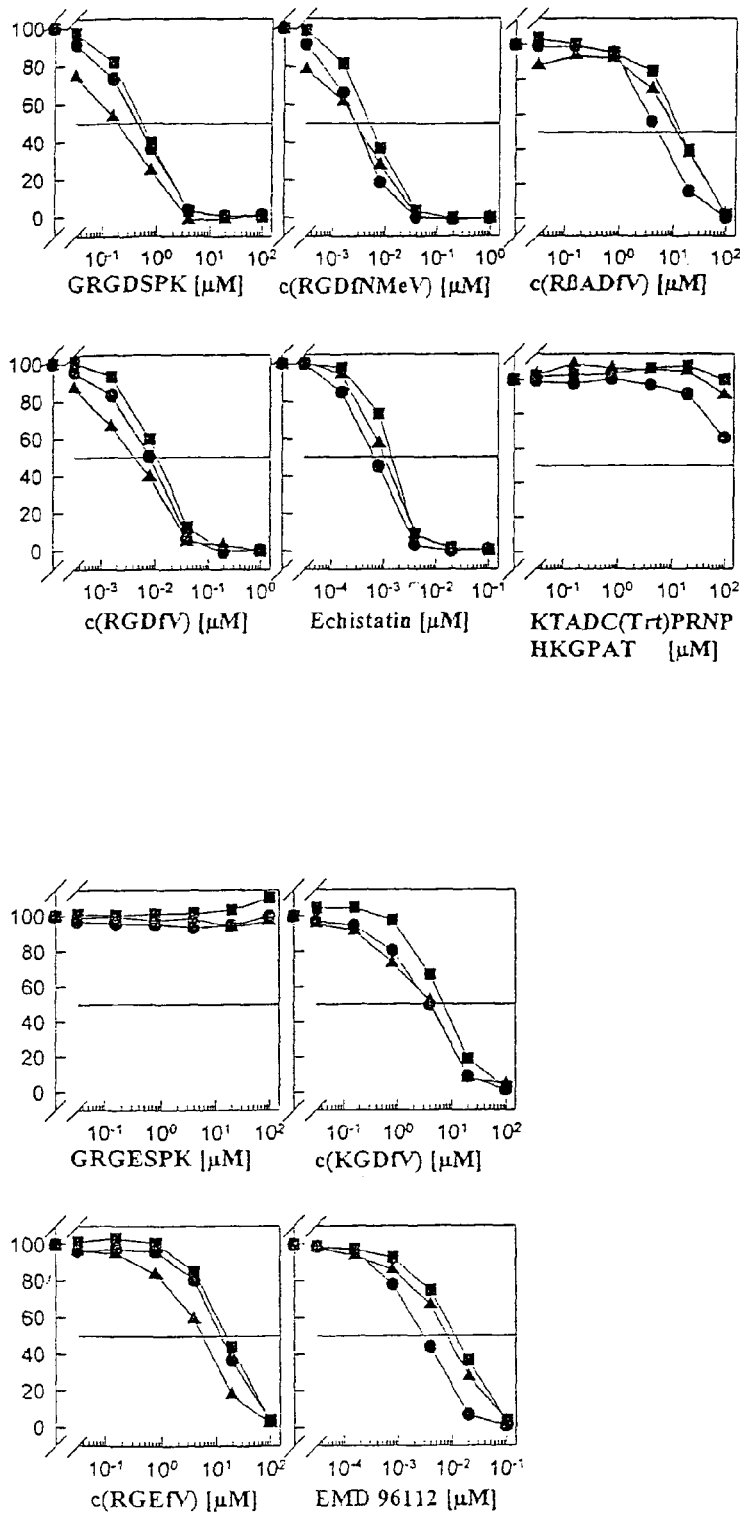

FIG. 8 shows effect of different RGD-peptides on vitronectin binding to different receptor preparations. Biotinylated vitronectin was incubated in parallel with increasing concentrations of several peptides as indicated. Vertical axis: VN binding % of control, horizontal axis: peptide concentration (SEQ ID NOS 1-3 are disclosed respectively in order of appearance);
-●-$\alpha_V\beta_3$ placenta
-■-$\alpha_V\beta_3$ recombinant truncated (1$^{st}$ preparing)
-▲-$\alpha_V\beta_3$ recombinant truncated (2$^{nd}$ preparing)

DETAILED DESCRIPTION

Microorganisms, cell lines, plasmids, phagemids, promoters, resistance markers, replication origins or other fragments of vectors which are mentioned in this application are normally commercially or otherwise generally available. In some cases the above-mentioned materials are not directly purchasable. However, they are used here only as examples in order to demonstrate properties or effects of the objects according to the invention, and are not essential to fulfill the requirements of disclosure. They can be replaced, as a rule, by other suitable generally obtainable tools and biological materials.

The invention includes also DNA and amino acid sequences having slightly varied or altered sequences or mutants and variants which can be obtained intentionally or randomly by chemical or physical processes. Generally, all such mutants and variants are included which show the described properties and functions.

The techniques and methods which are essential according to the invention are described in detail in the specification. Other techniques which are not described in detail correspond to known standard methods which are well known to a person skilled in the art, or are described more in detail in the cited references and patent applications and in the standard literature (e.g., Sambrook et al. 1989: Molecular Cloning, a laboratory manual, Cold Spring Harbor: Cold Spring Harbor Laboratory Press; Harlow and Lane 1988: Antibodies—A Laboratory Manual, Cold Spring Harbor: Cold Spring Harbor Laboratory Press).

Integrin $\alpha_V$ and $\beta_3$ cDNAs are known and available (e.g., Fitzgerald et al 1987, J. Biol. Chem. 262, 3936 ($\beta_3$) or Suzuki et al. 1987, J. Biol. Chem. 262, 14080 ($\alpha_V$)), or can be produced by known methods, for example, by nucleotide synthesizers.

The human $\alpha_V$ mature full-length protein chain according to the invention has 1018 amino acids, the transmembrane domain has approximately 29 amino acids and the cytoplasmic domain has approximately 32 amino acids. Cytoplasmic and transmembrane regions have about 61 amino acids. Cytoplasmic and transmembrane regions are located at the N-terminus of the chain. Thus, the preferred truncated $\alpha_V$ chain according to the invention has approximately 957 amino acids.

The human $\beta_3$ mature full-length protein chain according to the invention has 762 amino acids, the transmembrane domain has, like the $\alpha_V$ chain, approximately 29 amino acids and the cytoplasmic domain has approximately 41 amino acids. Cytoplasmic and transmembrane regions have, therefore, 70 amino acids. Cytoplasmic and transmembrane regions are located at the N-terminus of the chain. Thus, the preferred truncated $\beta_3$ chain according to the invention has approximately 692 amino acids.

According to the invention chains are preferred from which the complete cytoplasmic and transmembrane domain is removed. However, it is also possible to remove the complete cytoplasmic domain and only a portion of the amino acids of the transmembrane domain. Preferably, the truncated $\alpha_V$ or $\beta_3$ chain comprises additionally up 1 to 10 amino acids, especially 1 to 5 amino acids deriving from said transmembrane domain of each chain.

According to their nature the truncated $\alpha_V\beta_3$ receptor chains are glycosylated. The degree of glycosylation depends on their origin and the host cell system used.

The *baculovirus* expression system used according to the invention is also well known and commonly available. As a preferred *baculovirus* expression system, the BacPAK system from Clontech Laboratories, Inc. (supplied by Cambridge Bioscience, UK) is used. However, in principle, other *baculovirus* systems can be used.

According to the invention insect cells are infected with recombinant *baculovirus* DNA. In principal, all insect cell systems are suitable, however, those systems are preferred which guarantee a high infection by the virus system and a good and stable expression. Sf9 cells, and preferably High Five cells, which both are commercially available, are suitable insect cells. According to the invention, Sf9 cells are used according to the invention preferably for sub-cloning steps, whereas High Five cells are used, preferably for final expression steps (see Examples).

Sf9 cells (purchasable e.g. from Invitrogen Corporation) are, for example, maintained in TC100 supplemented with 10% insect cell-qualified Foetal Bovine Serum (FBS, Life Technologies, Inc.) and High Five cells (e.g. BTI-TN-5B1-4 from Invitrogen Corporation) are maintained, for example, in Express Five medium (Life Technologies, Inc.) supplemented with 16.5 mM L-Glutamine (Life Technologies, Inc.), Penicillin (50 IU/ml) and Streptomycin (50 µg/1 ml).

The generation of recombinant human $\alpha_V\beta_3$ receptor by means of a baculovirus-insect cell expression system is carried out, for example as follows:

The *baculovirus* system is used analogously to the methods given in Kidd and Emery (1993, Appl. Biochem. Biotechnol. 42, 137; O'Reilly et al., 1992: *Baculovirus* expression vectors: a laboratory manual. Oxford University Press, Inc., New York).

Figure 1:
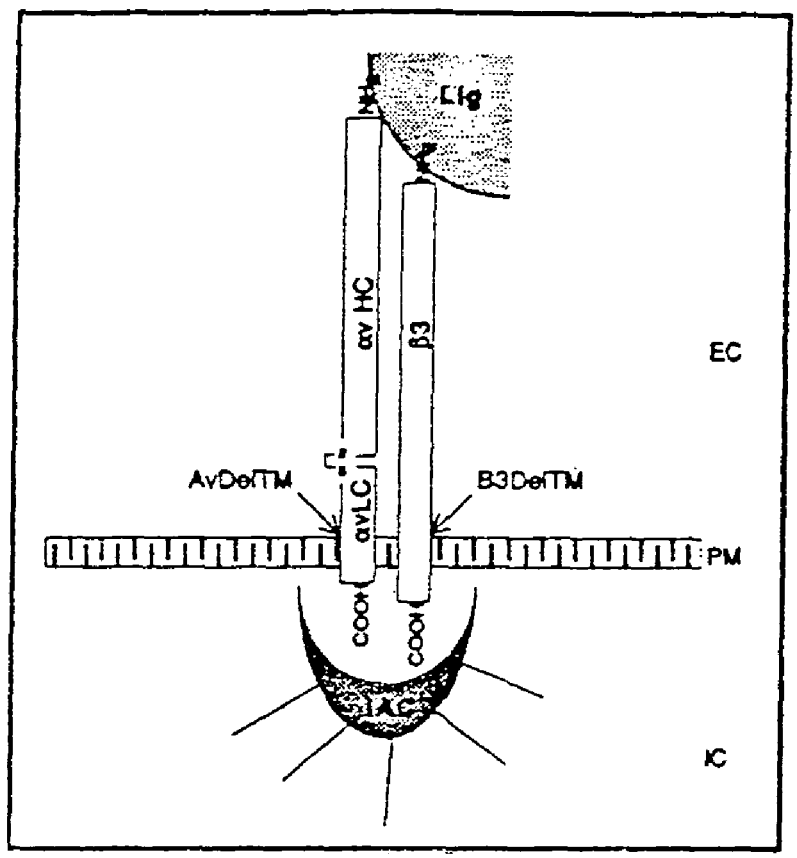
FIG. 1 shows a diagram of the $\alpha_V\beta_3$ heterodimer showing the sites for truncation of the $\alpha_V$ and $\beta_3$ chains. The $\alpha_V$ chain is normally post translationally cleaved into heavy ($\alpha_V$HC) and light ($\alpha_V$LC) chains that are linked with a disulfide (S—S) bond.
EC=Extracellular; PM=Plasma membrane; IC=Intracellular; IAC=Integrin Associated Cytoskeleton; Lig=Ligand

$\alpha_V$ and $\beta_3$ cDNAs truncated at positions coding for the transmembrane and extracellular interface (FIG. 1) are prepared by PCR. The $\alpha_V$ and $\beta_3$ truncated ($\alpha_V$(SL) and $\beta_3$(SL)) and the full length $\alpha_V$(FL) and $\beta_3$(FL) cDNAs are sub-cloned into *baculovirus* transfer vector pBacPAK9. It is also possible according to the invention to clone the cDNA of each chain into seperate vectors in order to avoid stability problems. However, cloning into one single vector is preferred, since this guarantees better that equimolar amounts of each chain are produced. Surprisingly, the present results show that the vector comprising the DNA sequences of both chains are, although rather large, stable enough.

The truncated ($\alpha_V$ and $\beta_3$ cDNAs usually comprise a signal sequence (thus, in case where the truncation comprises the complete transmembrane and cytoplasmic domain, coding for 987 $\alpha_V$ chain amino acids [957 for mature protein+30 for signal peptide] and 718 $\beta_3$ chain amino acids [692 for mature protein+26 for signal peptide]). Recombinant *baculovirus* expressing either full length or truncated $\alpha_V$ or $\beta_3$ chains are prepared by co-transfection with linearized *baculovirus* Bac-PAK6 genomic DNA followed by enrichment by plaque purification and virus amplification in Sf9 cells or High Five cells (O'Reilly et al., 1992: *Baculovirus* expression vectors: a laboratory manual. Oxford University Press, Inc., New York). Accurate integration of the transfer plasmids is confirmed by PCR and Southern blotting of the recombinant viral genomic DNA.

Figure 2:
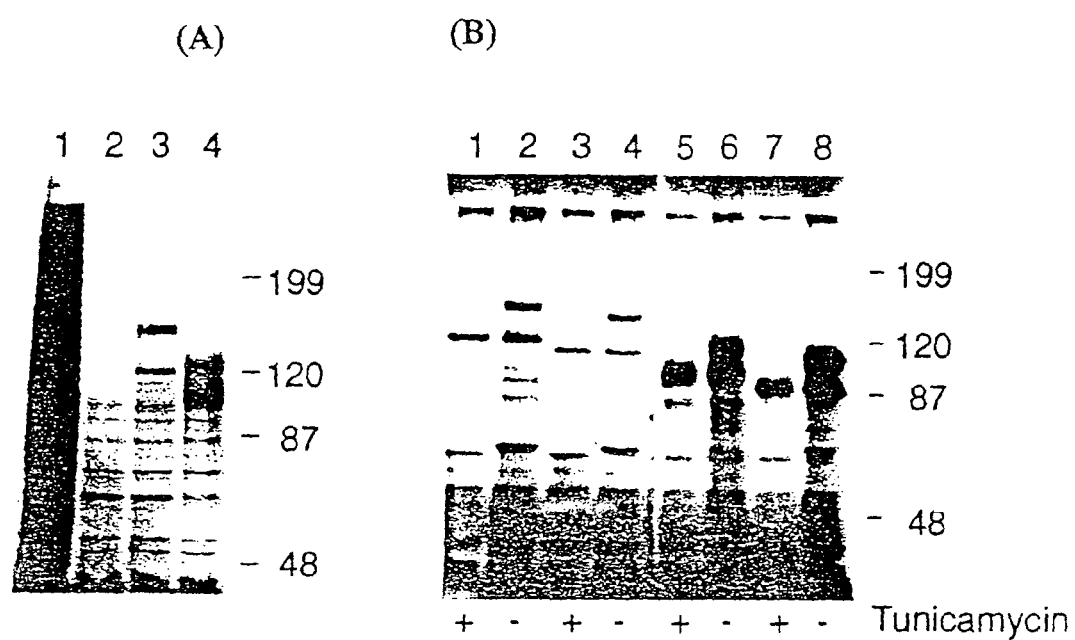
FIG. 2 shows
(A) Mock infected Sf9 cells (lane 1) or Sf9 cells infected with null recombinant (lane 2), $\alpha_V$ (FL) (lane 3) or $\beta_V$(FL) (lane 4) were metabolically labelled with $^{35}$S-labelled amino acids for 2 hours at 40 hours post infection. The cell extracts were resolved by SDS-PAGE under reducing conditions. The molecular mass in kDa of standard protein markers are indicated on the right.
(B) Sf9 cells infected with $\alpha_V$ (FL) (lanes 1 and 2), $\alpha_V$(SL) (lane 3 and 4), $\beta_3$ (FL) (lane 5 and 6) and $\beta_3$(SL) (lane 7 and 8) were either treated with 10 μM Tunicamycin in DMSO (lanes 1, 3, 5 and 7) or with DMSO alone (lanes 2, 4, 6 and 8). The infected cells were metabolically pulse labelled as above. Standard protein markers are indicated on the right.

Metabolic labelling of Sf9/High Five cells expressing full length $\alpha_V$ chain shows two major recombinant proteins of approximately 110 kDa and 150 kDa (FIG. 2A, lane 3). Similarly, Sf9 cells expressing full length $\beta_3$ how two bands of approximately 90 kDa and 125 kDa (FIG. 2A, lane 4). Comparison of mock infected (lane 1) and null recombinant virus infected (lane 2) also shows the degree of suppression of the host cell genome during the very late phase of the viral life cycle. Treatment of cells expressing either individual full length or truncated forms of $\alpha_V$ or $\beta_3$ with tunicamycin (FIG. 2B, lanes 1, 3, 5 and 7) inhibits the production of the slower migrating band, indicating that the 150/110 kDa bands (FIG. 2B, lanes 2 and 4) and the 125/90 kDa (FIG. 2B, lanes 6 and 8) correspond to glycosylated and unglycosylated forms of the recombinant proteins. This result confirms several reports that have suggested that the proportion of recombinant protein in *baculovirus* expression systems that undergo post-translational modifications, such as N-glycosylation, decreases during later stages of the virus life cycle (Jarvis and Finn 1995, Virology 212, 500). The relatively large difference in size between the glycosylated and unglycosylated forms of $\alpha_V$ and $\beta_3$ indicated that the proteins undergo substantial glycosylation, which is also in keeping with the presence in $\alpha_V$ of thirteen and in $\beta_3$ of ten potential N-glycosylation sites.

Figure 3:
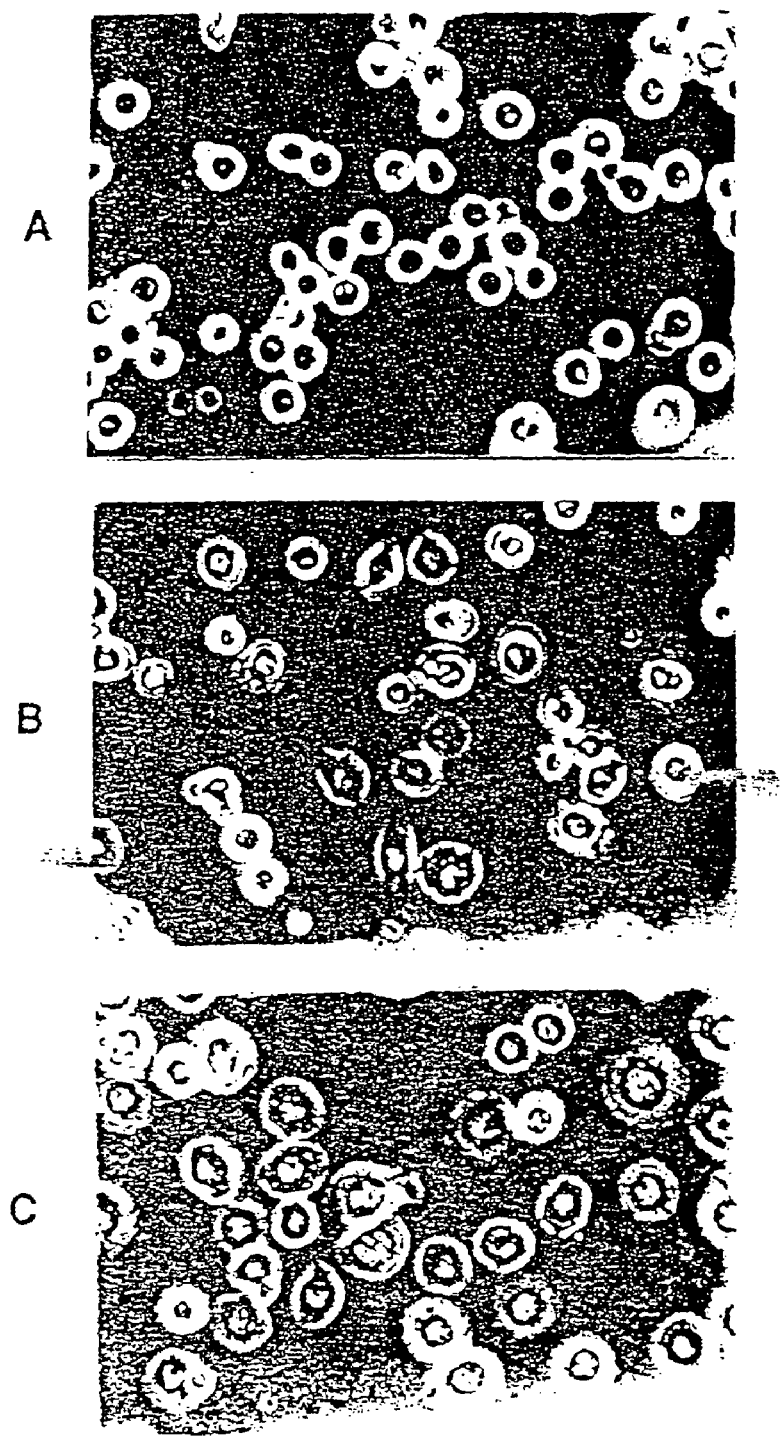
FIG. 3 shows cell shape change after co-infection. Sf9 cells infected with either null recombinant virus (A), $\alpha_V$(FL)+$\beta_3$ (FL) (B) or $\alpha_V$(SL)+$\beta_3$(SL) (C) at 48 hours post infection were photographed under phase contrast.

Integrins determine and modulate the cell shape by acting as structural links between the extracellular matrix and the cytoskeleton (Schwartz et al. 1995, Ann. Rev. Cell Dev. Biol. 11, 549; Montgomery et al. 1994, Proc. Natl. Acad. Sci. USA 91, 8856). In later phases of *baculovirus* infection, Sf9/High Five cells are usually rounded and loosely attached (FIG. 3A), as were the cells infected with either of the $\alpha_V$ or $\beta_3$ expressing recombinant *baculovirus* alone or with the null recombinant virus (FIG. 3A). However, insect cells co-infected with $\alpha_V$(FL)+$\beta_3$(FL) or $\alpha_V$(SL)+$\beta_3$(FL) are firmly attached and exhibit a more spread cell shape (FIGS. 3B and 3C). No shape change is observed in cells co-infected with $\alpha_V$(FL)+$\beta_3$(SL) or $\alpha_V$(SL)+$\beta_3$(SL). These results support the notion that the cytoplasmic domain of the $\alpha$-chain is responsible for negative regulation of the affinity for the cytoskeleton of the $\beta$-chain cytoplasmic domain (Filardo and Cheresh 1994, J. Biol. Chem. 269, 4641; Akiyama et al. 1994, J. Biol. Chem. 269, 15961; LaFlamme et al. 1994, J. Cell Biol. 126, 1287). $\alpha_V\beta_3$ binds many ligands that have the peptide sequence Arg-Gly-Asp (RGD). Correspondingly, cell shape change of $\alpha_V$ and $\beta_3$ virus infected Sf9 cells on vitronectin coated plates are inhibited when challenged with RGD peptides (Table 1).

TABLE 1

|  | − | +RGD | +nRGD |
|---|---|---|---|
| $\alpha_v$(FL) + $\beta_3$(FL) | ++ | − | ++ |
| $\alpha_v$(FL) + $\beta_3$(SL) | +/− | − | +/− |
| $\alpha_v$(SL) + $\beta_3$(FL) | +++ | − | +++ |
| $\alpha_v$(SL) + $\beta_3$(SL) | − | − | − |
| Null-Recombinant | − | − | − |

Control peptides, cyc(RGEfV) and cyc(RβADfV) where glutamate was substituted for aspartate, or β-alanine for glycine have no effect on cell shape.

Figure 4:
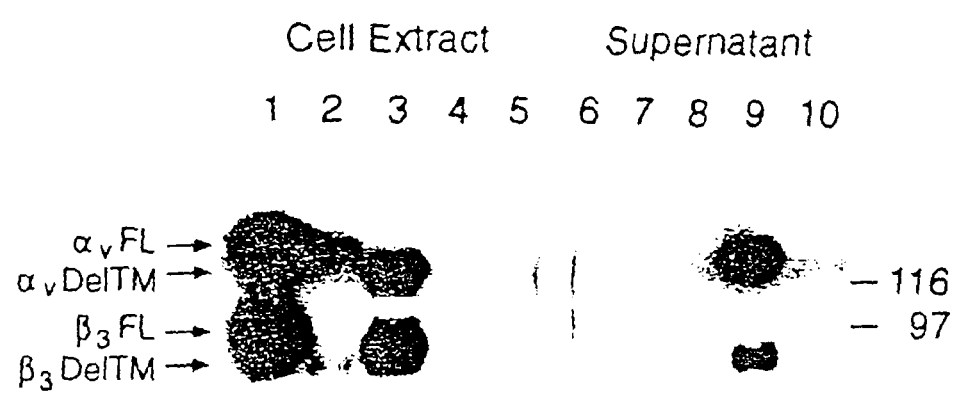
FIG. 4 shows immunoprecipitation of cell surface and soluble $\alpha_V\beta_3$. Cell extracts (lanes 1-5) and cell conditioned medium (lanes 6-10) prepared from High Five cells co-infected with $\alpha_V$(FL)+$\beta_3$(FL) (lanes 1 and 6), $\alpha_V$(FL)+$\beta_3$(SL) (lanes 2 and 7), $\alpha_V$(SL)+$\beta_3$(FL) (lanes 3 and 8), $\alpha_V$(SL)+$\beta_3$ (SL) (lanes 4 and 9) or null recombinant (lanes 5 and 10). $\alpha_V\beta_3$ complex was immunoprecipitated using monoclonal antibody LM609 and resolved by SDS-PAGE under non-reducing conditions, transferred onto PVDF membrane and detected with Streptavidin-HRP conjugate.

High Five cells, known to support higher level of production of *baculovirus* of expressed secreted proteins than Sf9 cells (Davis et al. 1993, In Vitro Cell Dev. Bio. Anim. 29A, 388), are co-infected with various combinations of recombinant *baculovirus* expressing the full length and truncated $\alpha_V$ and $\beta_3$. Immunoprecipitation of the $\alpha_V\beta_3$ complex with the MAb LM609 from cell extracts or from cell conditioned medium (FIG. 4) shows that the recombinant $\alpha_V\beta_3$ heterodimer is on the cell surface when either one or both the individual chains are full length (FIG. 4, lanes 1-3). More importantly, co-expression of truncated $\alpha_V$ with truncated $\beta_3$ results in secretion of a soluble heterodimer (FIG. 4, lane 9). Production of soluble $\alpha_V\beta_3$ in this serum free environment greatly simplified the downstream processing and also introduced a degree of flexibility in establishing large scale screening procedures for anti-$\alpha_V\beta_3$ compounds.

The novel truncated $\alpha_V\beta_3$ receptors according to the invention as well as their full-length variants are purified after recombinant expression by antibody affinity chromatography. Since the expression system according to the invention is very effective in producing large amounts of said receptor and only very small amounts of foreign proteins, and especially free from other human proteins, a single purification step is usually sufficient to obtain a highly purified product.

Antibody affinity chromatography is a well known technique: an antibody with a desired specificity to a certain antigen epitope is coupled enzymatically or chemically to a suitable activated support matrix, eg. modified agarose, sepharose, etc. Suitable antibodies according to the invention must have a good specificity to the $\alpha_V\beta_3$ receptor or to the single $\alpha_V$ chain or the single $\beta_3$ chain.

Many such antibodies are known, some of them are public domain antibodies and, therefore, without problems available. AP3 (anti-$\beta_3$), LM609 (anti-$\alpha_V \beta_3$), P4C10 (anti-$\beta_1$), P1F6 (anti-$\alpha_V\beta_5$) and 17E6 (anti-$\alpha_V$) have been characterized in detail (e.g., Mitjans et al. 1995, J. Cell Sci. 108, 2825). Monoclonal antibody 17E6 is an antibody which is produced by a hybridoma cell line having the designation 272-17E6. The cell line was deposited under accession number DSM ACC2160 at the Deutsche Sammlung für Mikroorganismen, Braunschweig, FRG. MAb 17E6 is, in addition, object of the European patent application 0 719 859. Anti-$\beta_3$ antibody AP3 is deposited at the ATCC under accession number HB-242. Antibodies 17E6 and AP3 are especially suitable according to the invention, because they are easily available. LM609 (Cheresh and Spiro 1987, J. Biol. Chem. 262, 17703) is also of special interest since it is directed to the alpha as well as to the beta chain.

After having coupled said antibody to the support, the clear cell-free medium of the infected and lysed insect cells, containing the truncated or the solubilized full-length recombinant receptor according to the invention, is applied to a column filled with said support, and is recirculated several times over the column to bind the expressed receptor to the immobilized antibody. The purified $\alpha_V\beta_3$ receptor is washed thereafter by means of an ionic buffer from the column and can be used directly for ligand binding and other experiments.

Human vitronectin, fibronectin and fibrinogen can be purified from human plasma (e.g., Yatohgo et, al. 1988, Cell Struct. Funct. 13, 281; Ruoslahti et al. 1982, Methods Enzymol 82 Pt A, 803; Ruoslahti 1988, Ann. Rev. Biochem. 57, 375; Kazal et al. 1963, Proc. Soc. Exp. Biol. Med. 113, 989).

In detail the purification and characterization of recombinant human $\alpha_V\beta_3$ is carried out for example, as follows:

Antibody affinity chromatography is carried out using 17E6, AP3 or LM609 antibodies. $\alpha_V\beta_3$ receptor from human placenta is, for example, purified by affinity chromatography according to the method of Smith and Cheresh (1988, J. Biol. Chem. 263, 18726).

Full length recombinant $\alpha_V\beta_3$ can be purified from non-ionic detergent solubilized extracts of High Five cells co-infected with $\alpha_V$(FL)+$\beta_3$(FL).

Soluble truncated $\alpha_V\beta_3$ can be purified from High Five cells co-infected with $\alpha_V$(SL)+$\beta_3$(SL) without using any detergent.

Figure 5:
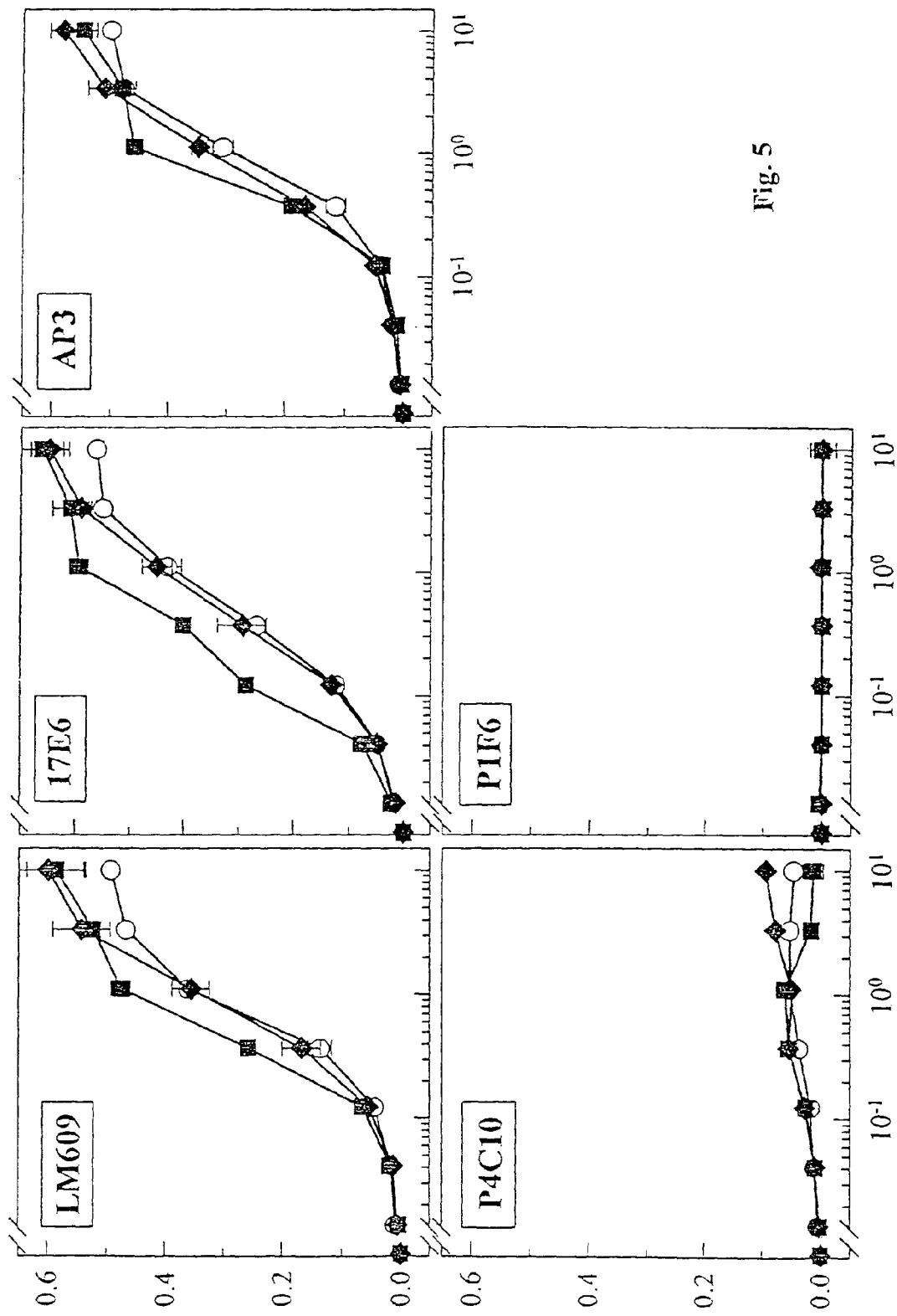
FIG. 5 shows analysis of purified receptors. Epitope and purity analysis of purified full length and truncated $\alpha_V\beta_3$ by monoclonal antibodies. Increasing receptor concentrations were immobilized and analyzed with antibodies LM609 (anti-$\alpha_V\beta_3$), 17E6 (anti-$\alpha_V$), AP3 (anti-$\beta_3$), P4C10 (anti-$\beta_1$) and P1F6 (anti-$\alpha_V\beta_5$). Vertical axis: optical density at 450 nm; horizontal axis: concentration of receptor coating (μg/ml).
(○) $\alpha_V\beta_3$ placenta, (■) $\alpha_V$(FL)×$\beta_3$(FL), (♦) $\alpha_V$(SL)×$\beta_3$(SL)

In ELISA, truncated soluble and full length solubilized recombinant $\alpha_V\beta_3$ are both recognized by the same antibodies (LM609, 17E6 and AP3) and with similar affinity, as judged by ELISA titres, as solubilized placental $\alpha_V\beta_3$. Each fails to react with anti-$\beta_1$ (P4C10) or with anti-$\alpha_V\beta_5$-specific (P1F6) antibodies indicating conservation of epitopes and low contamination with other integrins (FIG. 5).

Figure 6:
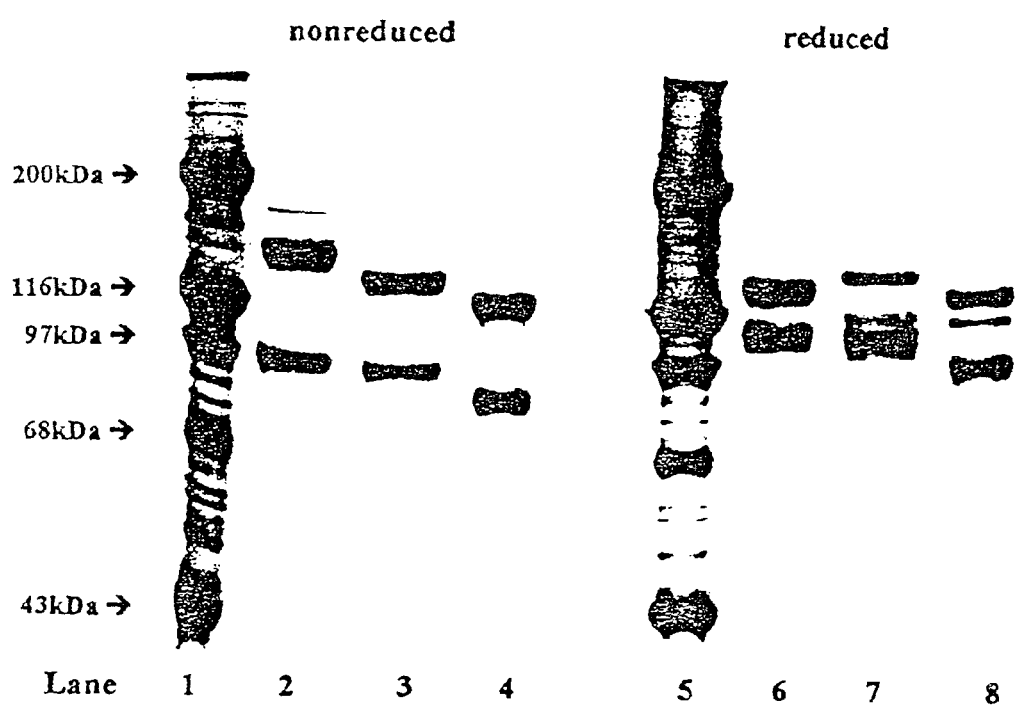
FIG. 6 shows analysis of purified receptors. Analysis of purified receptors by SDS-PAGE: Lane 1 and 5 HMW, lane 2 and 6 $\alpha_V\beta_3$ placenta, lane 3 and 7 $\alpha_V$(FL)×$\beta_3$(FL), lane 4 and 8 $\alpha_V$(SL)×$\beta_3$(SL). Lane 1, 3, 5, 7 are under nonreducing, lane 2, 4, 6, 8 are under reducing conditions.

Purified placenta $\alpha_V\beta_3$ dissociates into two bands of the $\alpha$-chain at 160 kDa and of the $\beta$-chain at 95 kDa when resolved by SDS-PAGE under non-reducing conditions (FIG. 6, lane 2). Purified full length recombinant $\alpha_V\beta_3$ (lane 3) dissociates into $\alpha_V$ chain of approximately 140 kDa and a $\beta_3$ chain at 90 kDa. The lower molecular weights may be due to incomplete or variant glycosylation of recombinant proteins expressed in *baculovirus* infected insect cells. Purified soluble recombinant $\alpha_V\beta_3$ dissociates into a truncated $\alpha_V$ chain of approximately 120 kDa and a truncated $\beta_3$ chain of 80 kDa.

The $\alpha_V$ chain normally undergoes post translational cleavage into heavy and light chains, linked by a disulfide bridge (FIG. 1) (Hynes 1992, Cell 69, 11). Therefore, under reducing conditions the $\alpha$ chain of placental $\alpha_V\beta_3$ further dissociates into the heavy chain of 140 kDa and the light chain of 25 kDa (FIG. 6, lane 6) while the $\beta$ chain migrates at 110 kDa. As the transmembrane truncation in the $\alpha$ chain lies within the light chain, both full length and truncated recombinant $\alpha$ chains should migrate under reducing conditions at ~140 kDa. However, the $\alpha_V$ chains of full length and soluble receptors exhibit the same molecular weights under both reducing and non-reducing conditions (lane 7 and 8), suggesting that there had only been partial post-translational cleavage of the $\alpha_V$ chain. The faint band of approximately 120 kDa in lanes 7 and 8 may represent the $\alpha_V$ heavy chain. This discrepancy between the placental and recombinant $\alpha_V\beta_3$ may be due to inefficient proteolytic processing during the very late phase of the *baculovirus* infection (O'Reilly et al. 1992, *Baculuvirus* Expression Vectors: A Laboratory Manual. Oxford University Press, Inc., New York).

TABLE 2 depicts an overview of the SDS-PAGE results:

| | human $\alpha_V\beta_3$ chains | kD (±10%) non-reduced | kD (±10%) reduced |
|---|---|---|---|
| Placenta | $\alpha_V$(FL) | 160 | 140 (hc), 25 (lc) |
| | $\beta_3$(FL) | 95 | 110 |
| recombinant | $\alpha_V$(FL) | 140 | 140 |
| | $\alpha_V$(SL) | 120 | 140 |
| | $\beta_3$(FL) | 90 | 105 |
| | $\beta_3$(SL) | 80 | 95 |

According to the process of the invention recombinant shortened $\alpha_V\beta_3$ receptor and full-length receptor can be prepared. In order to demonstrate that so-prepared receptors, above all the truncated form, show the ligand specifities of the natural receptor, which was isolated, e.g., from human placenta and used as comparison embodiment, a binding assay has to be established. Ligands known to be competitive inhibitors of the $\alpha_V\beta_3$ receptor are used therefor. As mentioned above, linear and cyclic peptides containing the RGD amino acid sequence (arginine-glycine-asparagine) are excellent inhibitors of said receptor.

Suitable peptides are, for example: GRGDSPK (SEQ ID NO: 1), Echistatin, cyclic-RGDfV, cyclic-RGDfNMeV, cyclic-R$\beta$ADfV, KTADC(Trt)PRNPHKGPAT (SEQ ID NO: 2), GRGESPK (SEQ ID NO: 3), cyclic-KGDfV, and cyclic-RGEfV. Additionally, also non-peptidic compounds which may mimick RGD-peptides and bind to the $\alpha_V\beta_3$ receptor can be used. Such RGD-peptides and non-peptidic analogues are, known (e.g. from European Appln. No. 96 113 972, European Publication Nos. 0578 083, 0632 053, 0478 363, 0710 657, 0741 133 and PCT Publication No. WO 94/12181) and/or can be synthesized by known standard methods. The ligands are modified by marker molecules or atoms according to methods known in the prior art. Preferably, biotinylated ligands are used.

The recombinant truncated $\alpha_V\beta_3$ receptor or its full-length version are immobilized, for example by adsorption at microtitre plates, and reacted with said marked ligands. The $\alpha_V\beta_3$ receptors according to the invention bind said ligands strongly, very similar to the natural receptor isolated from human placenta, whereas non-RGD peptides are not bound. This result demonstrates that the receptors, obtainable by the claimed process, are functionally intact with respect to their specific ligand binding capacity.

In detail, measurement of the biological activity of recombinant truncated $\alpha_V\beta_3$ receptor is carried out, for example, as follows:

The truncated and full length recombinant $\alpha_V\beta_3$ and placenta $\alpha_V\beta_3$ are immobilized and binding of biotinylated ligands is examined. Three purified RGD-containing ligands—vitronectin, fibrinogen and fibronectin—that are known to bind to $\alpha_V\beta_3$ are used. The ligands bind both to the full length and soluble receptor preparations in a concentration dependent manner, and with overlapping concentration dependencies and saturation concentrations similar to those of placental $\alpha_V\beta_3$ (FIG. 7). Vitronectin is used for testing specific interaction with the recombinant $\alpha_V\beta_3$. Biotinylated vitronectin and increasing concentrations of above-specified peptides or non-peptidic analogues are incubated in parallel with immobilized receptor. The compounds are able to inhibit vitronectin binding to placenta $\alpha_V\beta_3$ to full length and to soluble recombinant $\alpha_V\beta_3$ (FIG. 8) and are about 4-5 orders of magnitude more active than the $\beta$-alanine-to-glycine control peptide. Each receptor shows an $IC_{50}$-value for cyc(RGDfV) in the low nanomolar (1-5 nM) range.

In the same way as described here for known $\alpha_V\beta_3$ receptor specific ligands it is possible to screen for new drugs and therapeutic compounds which are regarded to be potent $\alpha_V\beta_3$ inhibitors.

This invention shows that the *baculovirus* insect cell expression system can be used to express high amounts of fully functional human recombinant $\alpha_V\beta_3$ integrins as soluble receptors secreted into the medium or, as alternative, on the cell surface. The double (SL)-truncated forms of the receptor are secreted as a complex into the medium as shown by precipitation and purification on an $\alpha_V\beta_3$-complex specific antibody (LM609, 17E6, AP3).

Under optimized conditions yields (soluble as well as full-length receptor) of 1-10 mg, preferably 2-5 mg/L culture medium (supernatant) can be obtained. This routine production in biochemical amounts of soluble $\alpha_V\beta_3$ opens the way for high throughput screening using $\alpha_V\beta_3$ and for structural analysis of this important receptor. The yield of natural receptor isolated from plancenta tissue is about 1-2 mg/kg tissue. Truncated and full-length recombinant $\alpha_V\beta_3$ proteins obtained by the process according to this invention have a purity of 95-99%, preferably 97-99%, as assessed by SDS-PAGE and ELISA. The soluble recombinant receptor is approximately 4-fold less sensitive to inhibitor than the full length recombinant molecules. A further advantage of the truncated soluble receptor is that it can be prepared without using detergents. The necessary non-ionic detergents are usually very expensive (e.g., ca. $500/10 g octyl-β-D-glyco-pyranoside). Approximately 25 g of detergent are necessary for solubilizing 3-4 mg receptor from placenta tissue.

Cells co-infected with recombinant virus with one full length and one truncated α- and β-chain ($\alpha_V$(FL)×$\beta_3$(SL) or $\alpha_V$(SL)×$\beta_3$(FL)) express hetero-dimeric receptor on their surface. But only cells containing either both full length chains, or full length β-chain and truncated α-chain show shape change when adhering on vitronectin. That this adhesion and spreading was $\alpha_V\beta_3$-specific was shown by adding RGD-containing peptides which specifically block the interaction between ligand and the native receptor while RGE- or RAD-peptides do not. Cells with full length α-chain and truncated β-chain do not spread.

ELISA shows that the $\beta_3$-specific antibody AP3 (Newman et al. 1985, Blood 65, 227) and $\alpha_V$-specific antibody 17E6 (Mitjans et al. 1995, J. Cell Sci. 108, 2825) and the complex-specific antibody LM609 (Cheresh and Spiro 1987, J. Biol. Chem. 262, 1770323) recognized both full length and truncated receptors, indicating that the recombinant integrins had the same epitopes as placenta $\alpha_V\beta_3$. SDS-PAGE shows under non-reducing conditions the bands typical for $\alpha_V$- and $\beta_3$-chains. The recombinant full length a chain has a lower molecular weight compared to the placenta full length a chain (approx. 140 kDa compared to 160 kDa) which could be explained by a decreased or different glycosylation in insect cells. Both full length and soluble recombinant $\alpha_V\beta_3$ receptors are able to specifically bind the ligands vitronectin, fibrinogen and fibronectin, the vitronectin binding was specifically inhibited by RGD-containing peptides with the same concentration dependency as the placental receptor.

With this demonstration of the specificity and similar saturation concentrations for ligand binding for full length and truncated human $\alpha_V\beta_3$ receptor it is now possible to embark on large scale preparation of functional recombinant soluble $\alpha_V\beta_3$ in the *baculovirus* insect cell system without the labor and the health risks associated using human placental tissue. Furthermore, the system described by this invention also allows expression of modified or chimeric receptors that could prove very useful for investigating at molecular level the ligand binding and the subsequent signal transduction processes.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding European application No. 96 119 700.1, filed Dec. 9, 1996 is hereby incorporated by reference.

EXAMPLES

Example 1

Construction of Recombinant Transfer Vectors $\alpha_V$ cDNA was excised as an EcoRI fragment from $\alpha_V$pcDNA-1Neo (Felding-Habermann 1992, J. Clin. Invest. 89, 2018) and cloned into the transfer plasmid pBacPAK8 (Clontech). The resulting recombinant was termed $\alpha_V$ (FL) (pBac8). The integrin $\beta_3$ cDNA was excised as a XbaI fragment from $\beta_3$pcDNA-1Neo and cloned into the transfer plasmid pBacPAK9 (Clontech). The transmembrane truncated $\alpha_V$ and $\beta_3$ cDNAs were constructed using Polymerase Chain Reaction (PCR) using Pfu Thermostable DNA polymerase (Stratagene). Truncated $\alpha_V$ cDNA coding for amino acids 1-987 of mature. ($\alpha_V$ (signal sequence included) was generated using oligonucleotide primers:
5'-GAC CAG CAT TTA CAG TGA-3' (SEQ ID NO: 4) [forward] and
5'CA CAG GTC TAG ACT ATG GCT GAA TGC CCC AGG-3' (SEQ ID NO: 5) [reverse Primer, containing translation stop codon (bold) after that coding for aa 987 followed by XbaI Restriction site (underlined)].

The PCR product was digested with SalI and XbaI restriction enzymes and the fragment was cloned into SalI/XbaI digested $\alpha_V$pcDNA-1Neo. The truncated $\alpha_V$cDNA was subcloned into EcoRI/XbaI sites of pBacPAC9 and the resulting clone was termed $\alpha_V$(SL) (pBac9). Truncated $\beta_3$ cDNA coding for aa 1-718 of mature $\beta_3$ (signal sequence includes) was generated using oligonucleotide primers:
5'-GCG CGC AAG CTT GCC GCC ACC ATG CGA GCG CGG CCG-3' (SEQ ID NO: 6) [forward primer containing the translation start codon (bold) and HindIII restriction site (underlined)] and 5'-GAT CGA TCT AGA CTA GGT CAG GGC CCT TGG GAC ACT-3' (SEQ ID NO: 7) [reverse primer also containing translation stop codon (bold) after that coding for aa 718 and XbaI restriction site (underlined)]. The PCR product was digested with HindIII and XbaI and cloned into HindIII/XbaI sites of pSK+ (Stratagene). The resulting clone, termed $\beta_3$(SL)(pSK+), was digested with HindIII and the ends were subsequently polished by filling in with Klenow fragment of DNA polymerase I (Boehringer Mannheim). The blunt-end linearized plasmid was then digested with XbaI restriction enzyme and the fragment was sub-cloned into SmaI/XbaI sites of pBacPAK9. The resulting clone was termed $\beta_3$(SL)(pBac9). The PCR amplified regions of both $\alpha_V$(SL)(pBac9) and $\beta_3$(SL)(pBac9) were verified by DNA sequencing and all the constructs were tested for expression of correct sized protein by in vitro transcription and translation from bacteriophage T7 promoter using TNT Coupled Reticulocyte Lysate System (Promega).

Example 2

Generation of Recombinant *Baculovirus*

BacPAK6 (Clontech) *baculovirus* genomic DNA was prepared from high titre virus stock (Page and Murphy 1990:

Methods in Molecular Biology. Humana Press, Clifton, N.J., USA) and linearized with Bsu36I (Kitts and Possee 1993, Biotechniques 14, 810).

Recombinant *baculovirus* clones expressing full length and truncated $\alpha_V$ and $\beta_3$ integrins were prepared according to the Clontech BacPAK product protocol. A null recombinant *baculovirus* clone was also prepared using pBacPAK9 as transfer plasmid for use as negative control. The correct recombinant viral clones were identified by PCR and the virus was propagated and titered in Sf9 cells (O'Reilly et al. 1992, *Baculuvirus* expression vectors: a laboratory manual. Oxford University Press, Inc., New York).

Example 3

Metabolic Pulse Labelling of Proteins Expressed in Sf9 Cells

Metabolic labelling of Sf9 cells was performed as described (Summer and Smith 1987: A manual of methods for *baculovirus* vectors and insect cell procedures. Texas Agricultural Experiment Station Bulletin B-1555). Where indicated, tunicamycin (Sigma) was present at 10 µg/ml for 16 hours before and during pulse labelling. Cells were lysed with 100 µl of buffer [1% Nonidet® P-40, 1 mM $CaCl_2$, 150 mM NaCl, 0.4 mM Pefabloc® (Boehringer Mann-heim), 10 µg/ml Leupeptin and E64 (Sigma), 10 mM Tris/HCl; pH 7.4; Nonidet P-40 is a detergent and Pefabloc is a protease inhibitor]. The lysate was centrifuged at 14000×g in an Eppendorf microfuge at 4° C. for 10 minutes and resolved by electrophoresis in 8% SDS-poly-acrylamide gel under reducing conditions, fixed, and dried before autoradiography (Sambrook et al. 1989 Molecular Cloning: A Laboratory Manual. Cold Spring Harbor Laboratory Press, Cold Sring Harbor, N.Y.).

Example 4

Protein Expression in Insect Cells

Recombinant proteins were expressed in High Five cells, either as monolayer or in suspension. Cells were co-infected with $\alpha_V$- and $\beta_3$-expressing recombinant *baculovirus*, each at M.O.I. of 5-20 (that means: one cell is infected with 5-20 virus DNA), in a minimum amount of medium with gentle agitation. After two hours the viral inoculum was removed and replaced with fresh Express Five medium, the infected cells were incubated at 27° C. for 48-64 hours. For isolation of membrane bound recombinant integrin, the cells were harvested by centrifugation (1000×g, 10 minutes) and the cell pellet was used. For isolation of the soluble recombinant integrin the cell-free supernatant was used.

Example 5

Immunoprecipitation

Immunoprecipitation of surface-biotinylated cell extract and cell conditioned medium was carried out with monoclonal antibody LM609 which recognises the extracellular domains of intact $\alpha_V\beta_3$-complex, linked to Affigel® beads (BIO-RAD) (Mitjans et al. 1995, J. Cell Sci. 108, 2825). After SDS-PAGE and Western blotting onto Hybond-PVDF membrane (Towbin et al. 1979, Proc. Natl. Acad. Sci. USA 76, 4350), the biotinylated proteins were detected by Enhanced-Chemiluminescence using ECL Western Blotting Detection Reagents (Amersham) as per manufacturers instructions.

Example 6

Cell Shape Change Studies

Sf9 cells (1×10$^6$ cells/well) were allowed to adhere to six-well plates either virgin or coated with purified human plasma vitronectin (5 µg/ml in PBS; 2 hours) followed by blocking of non-specific sites (3% BSA (w/v) in PBS), then infected with various virus combinations. The cells were observed 48 hours post-infection for cell shape change. Where indicated, the medium was supplemented with 10 µM cyclic peptides as competitive inhibitors of $\alpha_V$-integrin-ligand interaction [cyc (RGDfV), cyc(RβADfV) or cyc(RGEfV), where small letters are D-amino acids].

Example 7

Purification of Recombinant Integrins

High Five cells expressing full length $\alpha_V\beta_3$ were harvested, washed with PBS, and then lysed in ice cold lysis buffer [100 mM n-Octyl-β-D-glucoside, 1 mM $CaCl_2$, 2 mM Pefabloc in PBS, pH 7.4] for 1 h at 4° C. The lysate was centrifuged (10,000×g; 45 min at 4° C.) and the supernatant recirculated overnight at 4° C. over a 17E6-antibody affinity column pre-equilibrated with lysis buffer. After washing [20 ml bed volumes, 2×10 cm column, 50 mM n-Octyl-β-D-glucoside, 2 mM Pefabloc, 2 mM $CaCl_2$ in PBS, pH 7.4] bound protein was eluted [50 mM OG, 2 mM Pefabloc®, 2 mM $CaCl_2$, 50 mM Na-Acetate, pH 3.1], the eluant monitored at 280 nm, and the fractions were immediately neutralized (1:50 volume 3M Tris-HCl pH 8.8). Peak fractions were pooled, dialyzed [10 mM OG, 1 mM $CaCl_2$ in PBS, pH 7.4] and concentrated, then analyzed by SDS-PAGE. Aliquots at approx. 1 mg/ml protein were stored at −80° C. Protein concentration was determined against BSA standards with the BCA protein assay (Pierce).

Soluble truncated recombinant $\alpha_V\beta_3$ was purified by recirculating the cell free medium of infected High Five cells over an 17E6 affinity column at 4° C. The washing, elution and analysis were as described for the full length ($\alpha_V\beta_3$ except that no detergent was present in the buffers. ELISA analysis of the purified receptors used goat-anti-mouse IgG (H+L) HRP conjugate (BIO-RAD) and 3,3',5,5'-Tetramethylbenzidine-dihydrochloride (Sigma) as substrate.

Example 8

The purification of soluble and transmembrane full length $\alpha_V\beta_3$ receptor was achieved by using a LM609 antibody column.

Example 9

Preparation of an Antibody Affinity Chromatography Column

The support matrix (Affigel® BIORAD) was washed with 500 ml cold PBS. Purified antibody was incubated together with the support matrix (5 mg/ml gel) under circular rotation during ca. 12 hours. The supernatant was removed and still active groups on the matrix were blocked with 0.1 M ethanolamine. The support matrix was washed alternately several times with 0.01 M Tris-HCl pH 8.0 and 0.01 M sodium acetate pH 4.5 and was then directly used.

Example 10

Integrin Ligand Binding and Competition Assays: Biotinylation of Ligands or Antibodies Proteins in PBS were diluted with 5-fold concentrated ligation buffer [500 mM NaCl, 500 mM NaHCO$_3$] to 1 mg/ml protein. Freshly prepared N-hydroxysuccinimidobiotin (Sigma) [1 mg/ml in DMSO] was added to 0.1 mg/ml and incubated for 2 h at 20° C. After dialysis [PBS, 0.025% NaN$_3$], protein concentration was determined. The biotinylated proteins were stored at 4° C.

Ligand Binding assay Integrins were diluted to 1 µg/ml in coating buffer [150 mM NaCl, 1 mM CaCl$_2$, 1 mM MgCl$_2$, 10 µM MnCl$_2$, 20 mM Tris-HCl; pH 7.4) and 100 µl were adsorbed overnight at 4° C. to 96-well microtitre plates. The plates were washed once with binding buffer [0.1% (w/v) BSA in coating buffer] and blocked with blocking buffer (coating buffer containing 3% (w/v) BSA) 2 h at 37° C. After rinsing with binding buffer, serially diluted biotinylated ligands were added. After incubation (3 h, 37° C.), unbound ligand was washed from the plate with binding buffer, and bound biotin was detected by incubation with antibiotin-alkaline-phosphatase conjugated antibody and detection of bound antibody with p-Nitrophenyl-phosphate (BIO-RAD) substrate.

Example 11

Integrin Ligand Binding and Competition Assays: Competition Assays

Integrins were immobilized as described above. Serially diluted cyclic peptides were added in parallel with biotinylated vitronectin (1 µg/ml). After 3 h incubation at 37° C., bound ligand was detected as described above. Assays were performed in triplicate and repeated several times.

The preceding examples can be repeated with similar success by substituting the generically or specifically described reactants and/or operating conditions of this invention for those used in the preceding examples.

---

We claim:

1. A process for preparing a large amount of a purified soluble recombinant human $\alpha_V\beta_3$ adhesion receptor comprising an $\alpha_V$ chain and a $\beta_3$ chain and having substantially unimpaired ligand binding activity, comprising
   (i) subcloning
      (a) a first cDNA coding for the $\alpha_V$ chain of said receptor, truncated by a portion comprising at least 61 amino acids from the C-terminus of a mature human $\alpha_V$ protein comprising approximately 1018 amino acids, and
      (b) a second cDNA coding for the $\beta_3$ chain of said receptor, truncated by a portion comprising at least 70 amino acids from the C-terminus of a mature human $\beta_3$ protein chain comprising approximately 762 amino acids,
      into a baculovirus transfer vector of a baculovirus expression system,
   (ii) transferring said vector comprising said first and/or second DNA into the genomic DNA of a baculovirus of said expression system,
   (iii) infecting an insect cell with said complete recombinant baculovirus,
   (iv) cultivating said infected insect cells in a culture medium whereby said truncated $\alpha_V\beta_3$ receptor is expressed into the medium, and
   (v) purifying said expressed receptor from the medium by antibody affinity chromatography, wherein the antibody is specific to the human $\alpha_V\beta_3$ adhesion receptor or its individual component chains, wherein the cDNA of the truncated $\alpha_V$ chain is generated by PCR using the oligonucleotide primers 5'-GAC CAG CAT TTA CAG TGA-3' (SEQ ID NO: 4) and 5'-CA CAG GTC TAG ACT ATG GCT GAA TGC CCC AGG-3' (SEQ ID NO: 5), and the cDNA of the truncated $\beta_3$ chain is generated by PCR using the oligonucleotide primers 5'-GCG CGC AAG CTT GCC GCC ACC ATG CGA GCG CGG CCG-3' (SEQ ID NO: 6) and 5'GAT CGA TCT AGA CTA GGT CAG GGC CCT TGG GAC ACT-3' (SEQ ID NO: 7).

2. A process for preparing a large amount of a highly purified soluble recombinant human $\alpha_V\beta_3$ adhesion receptor which has substantially unimpaired ligand binding activity, comprising
   (i) subcloning into a baculovirus transfer vector of a baculovirus expression system
      (a) a first cDNA encoding the $\alpha_V$ chain of said receptor, shortened by a portion encoding 61 amino acids calculated from the C-terminus of a mature human $\alpha_V$ polypeptide of approximately 1018 amino acids, wherein said first cDNA is generated by PCR using the oligonucleotide primers 5'-GAC CAG CAT TTA CAG TGA-3' (SEQ ID NO: 4) and 5'-CA CAG GTC TAG ACT ATG GCT GAA TGC CCC AGG-3' (SEQ ID NO: 5), and (b) a second cDNA encoding the $\beta_3$ chain of said receptor, shortened by a portion encoding 70 amino acids starting at the C-terminus and of a mature human $\beta_3$ polypeptide of approximately 762 amino acids, wherein said second cDNA is generated by PCR using the oligonucleotide primers 5'-GCG CGC AAG CTT GCC GCC ACC ATG CGA GCG CGG CCG-3' (SEQ ID NO: 6) and 5'GAT CGA TCT AGA CTA GGT CAG GGC CCT TGG GAC ACT-3' (SEQ ID NO: 7), (ii) transferring said vector comprising said first and said second cDNA into the genomic DNA of a baculovirus of said expression system, (iii) infecting an insect cell with said complete recombinant baculovirus, (iv) cultivating said infected insect cells in a culture medium whereby said soluble $\alpha_v\beta_3$ receptor is expressed into the medium, and (v) purifying said expressed receptor from the medium.

3. The process of claim 1, wherein the first and second cDNA are sub-cloned into the same baculovirus vector.

4. The process of claim 1, wherein the baculovirus expression system is the BacPAK system.

5. The process of claim 1, wherein the insect cells infected are High Five (BTI-TN-5B1-4) cells.

6. The process of claim 1, wherein the specific antibody used for the antibody affinity chromatography is mAb 17E6 produced by a hybridoma cell line having the designation 272-17E6 (DSM ACC2160).

* * * * *

SEQUENCE LISTING

```
<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Arg Gly Asp Ser Pro Lys
 1               5

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Cys(Trt)

<400> SEQUENCE: 2

Lys Thr Ala Asp Cys Pro Arg Asn Pro His Lys Gly Pro Ala Thr
 1               5                   10                  15

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Arg Gly Glu Ser Pro Lys
 1               5

<210> SEQ ID NO 4
<211> LENGTH: 18
```

```
<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaccagcatt tacagtga                                                    18

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cacaggtcta gactatggct gaatgcccca gg                                    32

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcgcgcaagc ttgccgccac catgcgagcg cggccg                                36

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatcgatcta gactaggtca gggcccttgg gacact                                36
```